(12) United States Patent
Abe

(10) Patent No.: US 6,966,914 B2
(45) Date of Patent: Nov. 22, 2005

(54) RETRIEVAL CATHETER (75) Inventor: Bennett K. Abe, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 541 days.

(21) Appl. No.: 10/150,550

(22) Filed: May 16, 2002

(65) Prior Publication Data

US 2002/0188262 A1    Dec. 12, 2002

Related U.S. Application Data (60) Provisional application No. 60/291,277, filed on May 17, 2001.

(51) Int. Cl.[7] .............................................. A61B 17/22
(52) U.S. Cl. ...................................... 606/113; 606/106
(58) Field of Search ........................ 606/110–113, 200, 606/106

(56) References Cited

U.S. PATENT DOCUMENTS

| 5,108,406 | A |   | 4/1992  | Lee              |         |
|-----------|---|---|---------|------------------|---------|
| 5,171,233 | A |   | 12/1992 | Amplatz et al.   |         |
| 5,281,238 | A |   | 1/1994  | Chin et al.      |         |
| 5,562,678 | A | * | 10/1996 | Booker ........   | 606/113 |
| 5,741,271 | A |   | 4/1998  | Nakao et al.     |         |
| 6,015,415 | A |   | 1/2000  | Avellanet        |         |
| 6,068,603 | A | * | 5/2000  | Suzuki ........   | 606/113 |

* cited by examiner

*Primary Examiner*—Julian W. Woo
(74) *Attorney, Agent, or Firm*—Gary Baker; Quine Intellectual Property Law Group, P.C.

(57) ABSTRACT

This invention provides, e.g., a catheter with a threaded loop type snare tool for retrieval of objects from blood vessels and/or body cavities. The snare tool of the invention provides, e.g., independently maneuverable probe wires and snare wires to encircle and releasably snare foreign objects inside human and veterinary patients. The invention further provides methods of using the catheter of the invention to retrieve objects from patients.

22 Claims, 4 Drawing Sheets

RETRIEVAL CATHETER

CROSS-REFERENCE TO PRIOR APPLICATIONS

This application claims priority to and benefit of a prior U.S. provisional application No. 60/291,277, Retrieval Catheter by Bennett K. Abe filed May 17, 2001.

FIELD OF THE INVENTION

This invention is in the field of catheter medical devices. The present invention relates to, e.g., a retrieval catheter capable of snaring and removing foreign bodies from the vasculature or body cavities of human or veterinary patients. The retrieval catheter provides, e.g., a snare wire with an end loop that can be maneuvered around one side of an object and a probe wire that can be independently maneuvered around the other side and through the loop to form a snare to grasp the object.

BACKGROUND OF THE INVENTION

Medical technologies have provided a variety of devices to investigate and repair vascular maladies. For example, catheters are maneuvered up through the femoral artery and aorta to the heart for injection of radiological dyes, positioning of electrodes, or to install stents. Occasionally, foreign objects, such as loose stents, electrode leads and fragments of guide wires, are left in a blood vessel after a procedure. The objects must be removed, as they can result in sepsis, vessel blockage, infarction, or perforation of the vessel.

One approach to removing a foreign object from a vessel is surgery. An incision can be made in the body near the lodging site of the object and tissue dissected away until the object is reached and withdrawn. The tissues are then stitched back together and healing takes place over the course of several weeks. Such a procedure is not without risk. The surgery may require general anesthesia, with its inherent risks. Important vessels and nerves can be severed during resection of the tissues to reach the site. Infections can set in at the surgical site. Surgery is costly, and many sites are not readily accessible with open surgical methods.

Approaching the foreign object with a catheter through a blood vessel can be far less expensive and risky. A catheter, with some type of grasping or grappling tool tip can be fed through the vessel to the lodging site with the visual aid of a fluoroscope. At the lodging site, the tool is maneuvered into a position where it can secure a hold on the object. The catheter can then be withdrawn, the foreign object in tow. Difficulties can arise, however, when using current catheter tools in this retrieval task.

A hook style tool can be maneuvered around a foreign object in a vessel and used to drag the object out of the vessel. A disadvantage of the hook tool is that it can not reversibly grasp the end of an object. The hook works best in retrieving long flexible objects and objects with eyelets to receive the hook. If an attempt is made to retrieve a short object with a hook, it can slide down the object and slip off the end. Short stiff objects must be dragged along a vessel in a traverse orientation which can scrape or perforate vessel walls. The hook itself can become unreleasably entangled in objects or vessel walls.

Forceps style catheter tools are available with jaws that can open then clamp down to grasp an object. Such forceps design catheters require maneuvering room for the open mouth jaws to engage the object. The jaws do not surround the object, so they can slip away from the grasp. In some situations, prohibitively large designs may be required to provide an adequate grip.

The open loop snare tool is a fine loop that can constrict to grip the end of objects. For example, in U.S. Pat. No. 5,171,233, "Snare-Type Probe" to Amplatz, et al., a loop of wire is provided at the tip of a catheter which is maneuvered over an end of an object to be retrieved. Once the loop encircles the object, loop wires can be retracted into the bore of the catheter contracting the loop to provide a tight grasp of the object. But, if the end of the object is embedded in the wall of the vessel, the loop can not be maneuvered over the end to snare the object. Moreover, if the end of the object becomes lodged against a wall during withdraw, release of the tool may be difficult.

Another type of catheter snare tool is the threaded snare, e.g., as described in U.S. Pat. No. 5,562,678, "Needle's Eye Snare", to Booker. Here, a hook-shaped closed loop of superelastic wires is advanced from a catheter bore to curl around one side of an adjacent object. Next, a threader wire is advanced from the bore to extend around the other side of the object and between the wires of the loop. When the closed loop wires are withdrawn into the catheter bore, the object is captured in a contracting snare. Such a catheter tool is capable of capturing an object in a snare even if no free end is available. In addition, the hook and threader can be independently advanced and retracted, allowing ready release by retracting the threader, should the object become immovable. Still, difficulties remain in maneuvering the large double wire hook around objects of different shapes and orientations as it advances in a superelastic shape memory curl from the catheter bore. Maneuvering the threader wire can also be difficult since it is not rotatable independent of the hook. Furthermore the large expensive superelastic loop can be difficult to securely assemble onto a positioning wire do to peculiarities of the superelastic material.

In view of the above, a need exists for a catheter snare tool with the small size and versatile maneuverability required to surround foreign objects with diverse shapes and orientations. Benefits could also be realized through catheter snare tool technologies that cost less and are easier to manufacture. The present invention provides these and other features that will be apparent upon review of the following.

SUMMARY OF THE INVENTION

The present invention provides, e.g., a retrieval catheter with a releasable snare tool composed of a maneuverable snare wire with an end loop and an independently maneuverable probe wire. Angles in the wires allow, e.g., selection of advancement routes by rotation to maneuver around complex topography before intersecting to form a snare. The invention provides methods to retrieve objects with the catheter.

The retrieval catheter of the invention can include, e.g., a tube-shaped member, adapted for insertion into a patient, having a first lumen extending through to a distal port and slidably retaining a snare wire with a first angle and an end loop, and a second lumen extending through to a proximal port and slidably retaining a probe wire. The tube-shaped member can be fabricated from, e.g., plastic or composite materials. The snare wire and probe wire can be independently advanced, retracted and/or rotated to make maneuvers independent of each other.

The retrieval catheter of the invention can have, e.g., an alignment region with a second angle near the proximal port, thereby offsetting the distal port relative to the proximal port. The second angle can range, e.g., from about 0 degrees and about 180 degrees. The alignment region can be, e.g., fabricated from a resilient material to allow flexion and extension of the second angle. The alignment region of the tube-shaped member can, e.g., have a third lumen extending through it, and an alignment wire slidably retained in the third lumen, whereby the alignment wire can be advanced to force the second angle open to about 180 degrees.

The snare wire of the invention can be fabricated from, e.g., stainless steel and have a first angle between about 90 degrees and about 180 degrees. The snare wire can have, e.g., an end loop made of a stainless steel, gold, platinum, and/or superelastic shape memory alloy (such as nickel-titanium) and have a diameter ranging from about 0.01 inches to about 0.2 inches. A superelastic end loop can have, e.g., a collapsed shape when retained within the first lumen and an elliptical shape when outside of the lumen.

The probe wire can be fabricated from, e.g., stainless steel, or other metal alloys, and have a third angle between about 90 degrees and about 180 degrees. The probe wire can have a diameter ranging from about 0.01 inches to about 0.2 inches.

The retrieval catheter of the invention can be, e.g., configured such that an object can be retrieved from the body of a patient by positioning the tube-shaped member near the object, forming a snare around the object with the wire tools, grasping the object and pulling the object out of the patient. For example, the distal port of the tube-shaped member is positioned adjacent to the object and the snare wire end loop is advanced from the first lumen. The snare wire is maneuvered around one side of the object. The probe wire can then be advanced from the second lumen and maneuvered around the other side of the object. The probe wire is maneuvered further through the snare wire end loop to form a snare. The snare wire is retracted into the first lumen to constrict the snare around the object to grasp the object. Finally, the tube-shaped member is withdrawn from the patient to retrieve the object from the patient.

The method of using the retrieval catheter of the invention can include independently maneuvering the wires to surround the object to form a snare that can grasp the object. For example, a tube-shaped member, which retains a probe wire, and a snare wire with an angled region and an end loop, is inserted into the patient. The tube-shaped member is positioned with the snare wire and probe wire adjacent to the object. The snare wire is axially rotated and advanced around one side of the object. The probe wire is independently advanced around a second side of the object and through the end loop of the snare wire to form a snare. The snare wire is retracted into the tube-shaped member to constrict the snare, thereby grasping the object. The probe wire can have, e.g., a third angle to aid in maneuvering it into the end loop of the snare wire. The snare can be constricted, e.g., by retracting the snare wire or by holding the snare wire stationary while the tube-shaped member is advanced toward the object. After the object is grasped, it can be withdrawn, e.g., by retracting the tube-shaped member from the patient, thereby retrieving the object.

The object retrieval method of the invention can be, e.g., used to remove a foreign object from the vasculature or body cavity of a human patient or veterinary patient.

DETAILED DESCRIPTION

The present invention provides, e.g., a releasable snare type retrieval catheter having a snare wire maneuverable around one side of an object, and a probe wire independently maneuverable around the other side and through an end loop of the snare wire, to form a snare. The wires are, e.g., slidably retained in lumens which allow individual advancement and rotation of the wires. The methods of the invention provide, e.g., techniques to capture and retrieve foreign objects from human or veterinary patients using catheters of the invention.

Figures 1A, 1B:
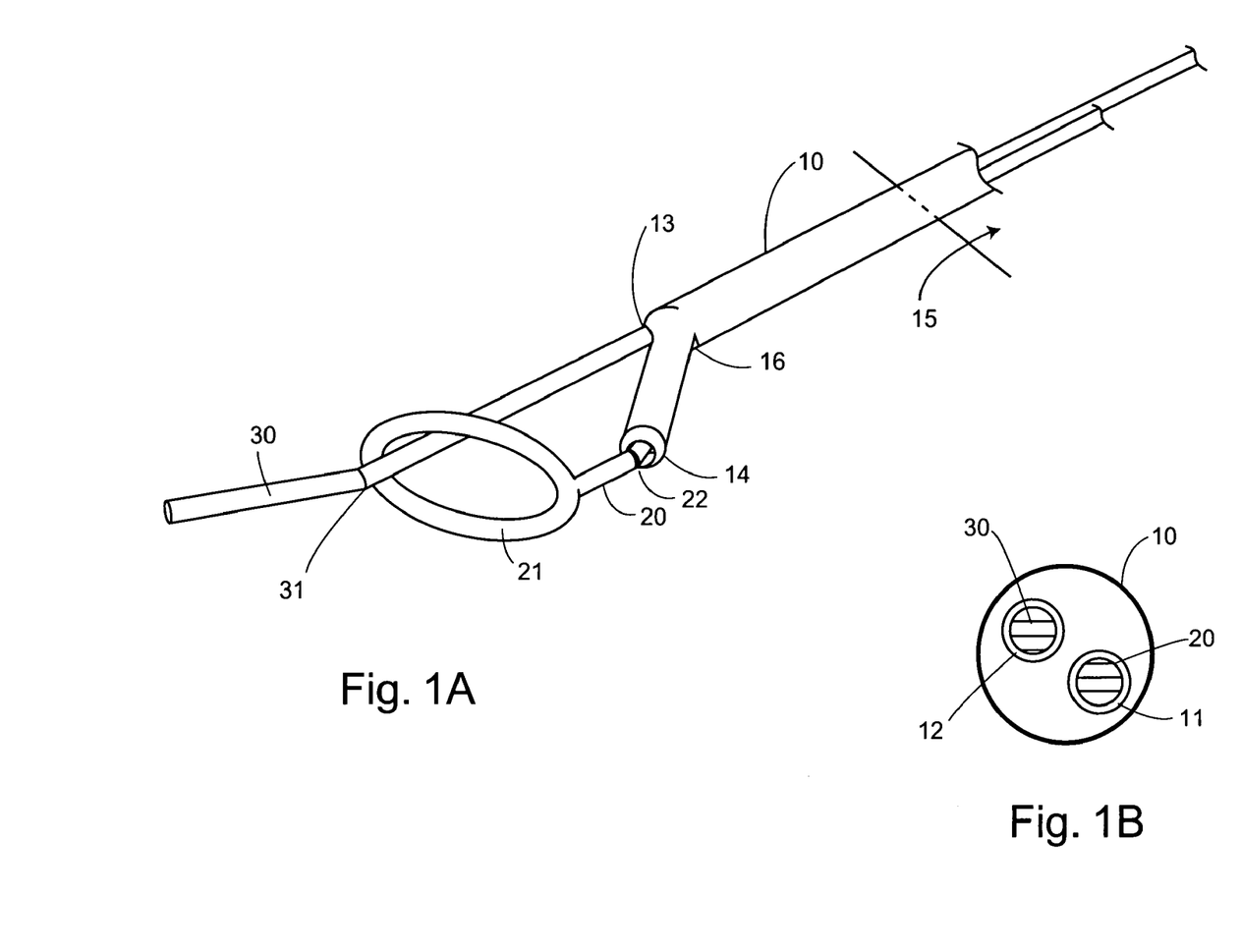
FIGS. 1A and 1B are schematic diagrams of a retrieval catheter configured as a snare.

An exemplary embodiment of the retrieval catheter is presented in FIGS. 1A and 1B. Tube-shaped member 10 has first lumen 11 that slidably retains snare wire 20 and second lumen 12 that slidably retains probe wire 30. In use, a snare can be formed, as shown in FIG. 1A, with probe wire 30 threaded through snare wire end loop 21.

The Tube-Shaped Member

The tube-shaped member (TSM) is, e.g., a structure used to insert catheter tools (i.e., the snare wire and probe wire) into the body of a patient and to position the tools at the lodging site of a foreign object. The TSM, e.g., houses lumens which retain the wires with freedom to advance and rotate as they maneuver around and snare the object. Ultimately, e.g., the withdrawal of the TSM from the patient's body retrieves the snared object from the lodging site.

The TSM is adapted for insertion into the body of a patient. For example, the TSM can have a diameter narrow enough to navigate the insertion route, such as a blood vessel, gland duct, and/or body cavity, without causing injury to tissues along the route. The TSM can be flexible enough, e.g., to slide and rotate along the route between the body entry incision and the object lodging site without undue stress on adjacent tissues. The TSM outer surface is typically smooth, without any unnecessary protrusions. The TSM can be, e.g., fabricated from biocompatible and sterilizable materials, such as polyurethane, polyethylene, polypropylene, teflon, nylon, or polyvinylchloride.

The proximate end 15 of the TSM, which typically remains outside the body of the patient, can include, e.g., a hand grip section for a surgeon or other appropriate person to advance, retract and/or rotate the catheter during retrieval procedures. Proximal sections of the snare wire, probe wire and/or alignment wire, e.g., can extend out from their respective lumens to present hand grips for a surgeon to control advancement and/or rotation of the wires, as appropriate. It can be appreciated by those in the art that computer controlled and/or motorized mechanisms, e.g., can be adapted to provide wire control functions.

First lumen 11 of TSM 10 retains snare wire 20 and extends, e.g., from the proximal end of the TSM to distal port 14 at the distal end of the TSM. First lumen 11 can have a diameter, e.g., wide enough to provide adequate clearance between the lumen wall and snare wire 20 for unrestricted wire flexion, axial movement, and rotation. The lumen walls can, e.g., be made of a low friction material and/or have a lubricated surface to increase the precision of movement and to reduce the forces required to manipulate snare wire 20.

Second lumen 12 of TSM 10 retains probe wire 30 and can, e.g., extend from the proximal end of the TSM to proximal port 13 adjacent to distal port 14 of the TSM. The internal diameter of second lumen 12 can be, e.g., wide enough to provide adequate clearance between the lumen wall and probe wire 30 for unrestricted wire flexion, axial movement, and rotation. The lumen walls can, e.g., have a lubricated surface and/or be made from a low friction material, to increase the precision of movement and reduce the forces required to manipulate probe wire 30.

Second angle 16 can be provided, e.g., in the region of proximal port 13 to offset distal port 14 from the main axis of the TSM, thus separating the initial points of advancement of snare wire 20 and probe wire 30 relative to the object. Second angle 16 can range, e.g., from about 0 degrees to about 180 degrees, e.g., from about 0 degrees to about 45 degrees, or about 130 degrees to about 180 degrees. The separated wires provide, e.g., a better orientation for maneuvering the wires around some relatively large objects.

Figures 3A, 3B:
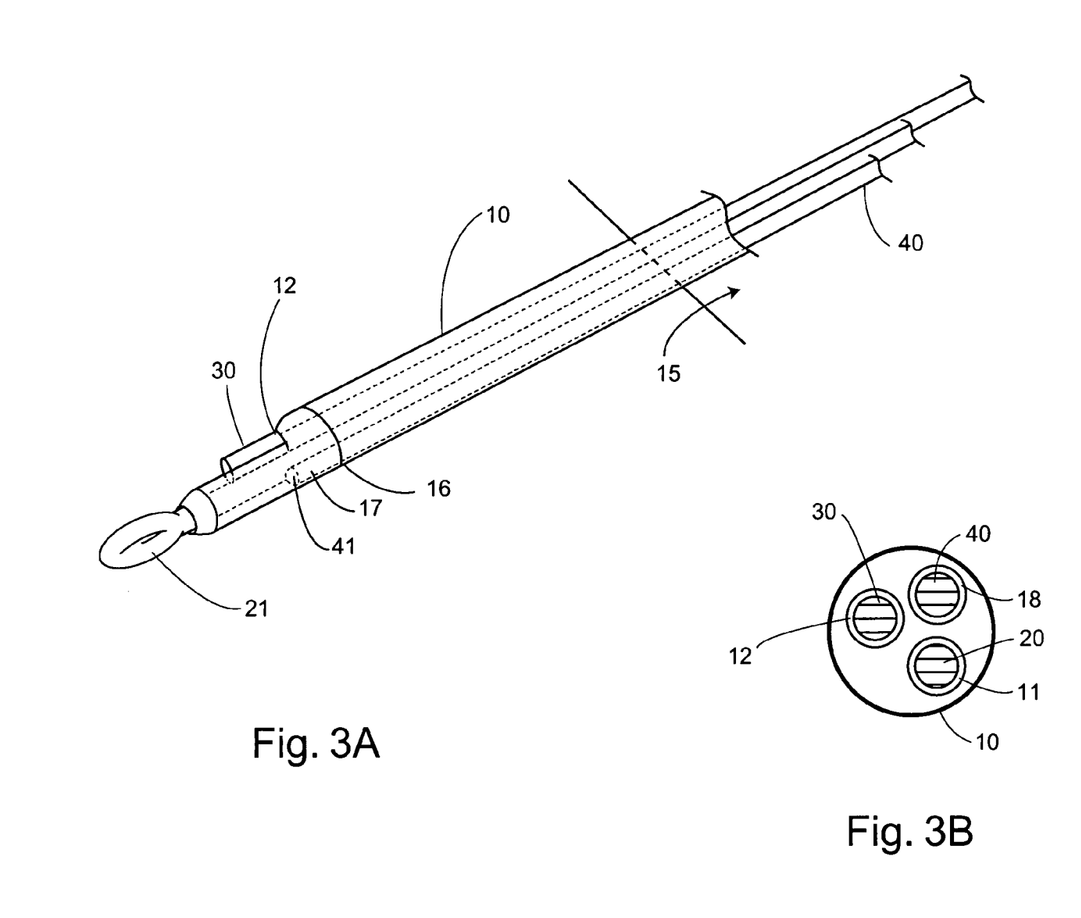
FIGS. 3A and 3B are schematic diagrams of a retrieval catheter with an alignment wire advanced into an alignment region to straighten the second angle.

Resilient alignment region 17, can be provided, e.g., to allow adjustment of second angle 16 (see, FIGS. 3A and 3B). Third lumen 18 can retain alignment wire 40, and extend, e.g., from the proximal end of TSM 10 to a position in alignment region 17, or beyond. The internal diameter of third lumen 18 can be, e.g., wide enough to allow smooth advancement and retraction of alignment wire 40. The lumen walls can be made from, e.g., a low friction and/or abrasion resistant material to facilitate the TSM alignment function, wherein straight alignment wire 40 is forced along third lumen 18 into angled alignment region 17.

The Snare Wire

Snare wire 20 of the invention can include, e.g., end loop 21 and first angle 22. Snare wire 20 can be, e.g., slidably retained in first lumen 11 of TSM 10 and can advance from distal port 14. The proximal end of the snare wire can extend, e.g., out from the proximal end of the TSM to provide advancement and rotation control by a surgeon and/or adapted instrumentation.

In one embodiment, the end loop of the invention can be, e.g., a small loop, just large enough to receive the probe wire to form a snare. In a retracted configuration of the snare wire, the end loop can, e.g., rest just outside the distal port or be received inside the distal port. The end loop of this embodiment can be, e.g., fabricated form the same material, such as stainless steel, as the remainder of the snare wire.

Figure 2:
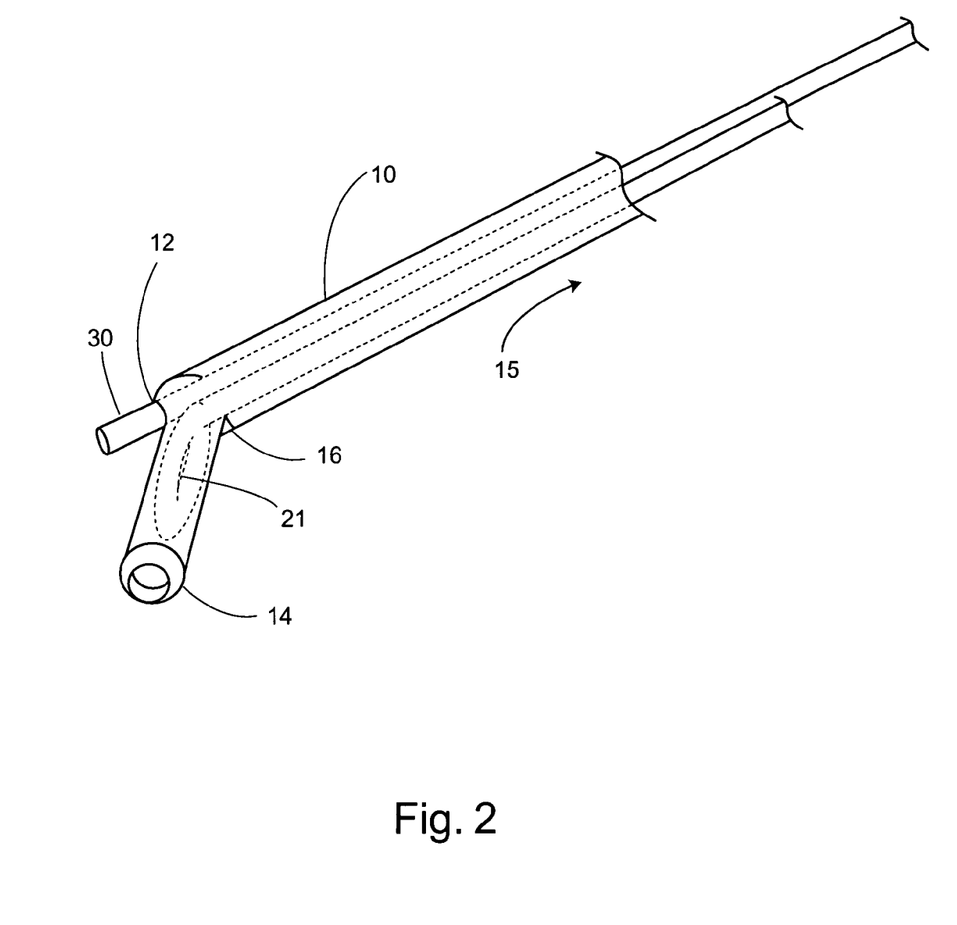
FIG. 2 is a schematic diagram of a retrieval catheter with a superelastic snare wire end loop retracted within the lumen of the tube-shaped member in a collapsed configuration.

In another embodiment, e.g., shown in FIG. 2, end loop 21 of the invention can be a loop of superelastic shape memory alloy, such as a nickel-titanium alloy. In a retracted configuration of snare wire 20, superelastic end loop 21 can, e.g., be retained within first lumen 11 in a collapsed shape. In a configuration with the snare wire advanced, the end loop can, e.g., take on an elliptical shape outside of the lumen. Such an arrangement can, e.g., allow a large end loop to be positioned in constricted spaces. A larger loop can have the advantage of, e.g., being easier to thread with the probe wire (but more difficult to maneuver around objects).

Snare wire 20 of the invention can have, e.g., first angle 22 to incline end loop 21 for enhanced maneuverability as snare wire 20 is advanced around an object. The first angle can be located, e.g., at and/or before the juncture of the end loop with the main part of the snare wire. The first angle can be, e.g., from about 90 degrees to about 180 degrees. As the snare wire is axially rotated, the end loop describes a circle.

As a surgeon advances the snare wire around an object, the end loop can be, e.g., rotated to points in the circle for selection of a route and/or to avoid obstacles. After the snare wire has been maneuvered around the object, the first angle, e.g., allows the end loop to be cooperatively presented for threading by the probe wire.

The proximal end of the snare wire can, e.g., extend out of the first lumen from the proximal end of the TSM for control interactions. The proximal end of the snare wire can be provided, e.g., with a knurled hand grip for a surgeon to hold while advancing, retracting, and/or rotating the snare wire. Such manipulations would, of course, be reflected in corresponding maneuvers of the end loop at the distal end of the snare wire. Motorized and/or computerized instrumentation can be attached to the snare wire and adapted, as is understood in the art, to carry out the mechanical control functions.

The snare wire can be, e.g., fabricated from material, such as stainless steel, with the strength and flexibility to advance, retract, rotate and flex in the contorted confines of the lumen during an object retrieval procedure. The snare wire can be, e.g., flexible enough for the first angle to be withdrawn into the first lumen, in a straightened configuration, yet return to approximately the original angle after advancement out of the lumen.

The catheter, e.g., with the narrowest TSM able to perform a particular retrieval procedure, should be used to allow smooth manipulation of the TSM and avoid injury to surrounding tissue. Smaller wires allow for a smaller TSM. The snare wire of the invention can have a diameter, e.g., from about 0.01 inches to about 0.2 inches. Smaller wires, e.g., from less than about 0.01 inches to about 0.05 inches, can be used to retrieve objects from small blood vessels, such as small branches of coronary arteries. Larger wires, e.g., from about 0.5 to more than about 0.2 inches, can be used to retrieve objects from inside body cavities, such as the urinary bladder.

The Probe Wire

Probe wire 30 of the invention can be, e.g., slidably retained in second lumen 12 of TSM 10, and can advance and rotate from proximal port 13. Probe wire 30 can include, e.g., third angle 31 to provide enhanced maneuverability. A proximal end of the probe wire can extend, e.g., out from the proximal end of the TSM to provide advancement and rotation control by a surgeon and/or adapted instrumentation.

Probe wire 30 of the invention can have, e.g., third angle 31 to incline the probe distal end for enhanced maneuverability as the probe wire is advanced around an object. The third angle can be located, e.g., an appropriate distance from the probe distal end, such as from about 0.01 inches to about 5 inches, depending on the scale of the object and lodging site. The third angle can be, e.g., from about 90 degrees to about 180 degrees. As a probe wire with a third angle is axially rotated, the probe distal end describes a circle. As a surgeon advances the probe wire around an object, the probe distal end can be, e.g., rotated to points in the circle for selection of a route and/or to avoid obstacles. After the probe wire has been maneuvered around the object, the third angle, e.g., facilitates maneuvering of the probe distal end into the snare wire end loop to form the snare.

The proximal end of the probe wire can, e.g., extend out of the second lumen from the proximal end of the TSM for control interactions. The proximal end of the probe wire can be provided, e.g., with a knurled hand grip for a surgeon to hold while advancing, retracting, and/or rotating the probe wire. Such manipulations are reflected, e.g., in corresponding maneuvers of the end loop at the distal end of the probe wire. Motorized and/or computerized instrumentation can be attached to the probe wire and adapted, as is understood in the art, to carry out the mechanical control functions.

The probe wire can be, e.g., fabricated from material, such as stainless steel, platinum, gold, or metal alloys such as nitinol, with the strength and flexibility to advance, retract, rotate, and flex, in the contorted confines of the lumen during an object retrieval procedure. Probe wire materials can be selected, e.g., to provide resistance to kinking and improve radiopacity for fluoroscopic viewing. The wire can be, e.g., covered with a biocompatible hydrophilic lubricant coating to reduce the amount of force required to manipulate the tool. The probe wire can have a diameter, e.g., from about 0.01 inches to about 0.2 inches. The probe wire can be, e.g., flexible enough that the third angle can be withdrawn into the second lumen in a straightened configuration yet return to approximately the original angle after advancement out of the lumen.

The Alignment Wire

Alignment wire 40 of the invention can be, e.g., slidably retained in third lumen 18 of TSM 10 (see, FIGS. 3A and 3B). The proximal end of the alignment wire can extend, e.g., out from the proximal end of the TSM to provide advancement control by a surgeon and/or adapted instrumentation.

Alignment tip 41, on the distal end of alignment wire 40, can be, e.g., adapted for forcing second angle 16 into alignment. Alignment tip 41 can be, e.g., rounded or wedge-shaped, to provide a smooth application of force along the inside of third lumen 18 during TSM alignment procedures. For example, before insertion or withdrawal of TSM 10, the surgeon can, e.g., advance alignment wire 40 into alignment region 17 along third lumen 18. As alignment wire 40 enters the angled portion of alignment region 17, rounded alignment tip 41 can contact the wall of third lumen 18 without abrasion or perforation as second angle 16 of the TSM is forced into an angle of about 180 degrees.

The proximal end of the alignment wire can, e.g., extend out of the third lumen from the proximal end of the TSM for control interactions. The proximal end of the alignment wire can be provided, e.g., with a knurled hand grip for a surgeon to hold while advancing or retracting the alignment wire. Motorized and/or computerized instrumentation can be attached to the alignment wire and adapted, as is understood in the art, to carry out the mechanical control functions.

The alignment wire can be, e.g., fabricated from material, such as stainless steel, platinum, gold, or metal alloy, with the strength and flexibility to advance, retract, and flex, in the contorted confines of the third lumen during an object retrieval procedure. The alignment wire can have a diameter, e.g., from about 0.01 inches to about 0.2 inches.

The Object Retrieval Methods

The methods of the invention to retrieve objects include, e.g., positioning catheter tools adjacent to an object, maneuvering the tools around the object to form a snare, constricting the snare to grasp the object, and withdrawing the catheter to retrieve the object.

Figure 4A:
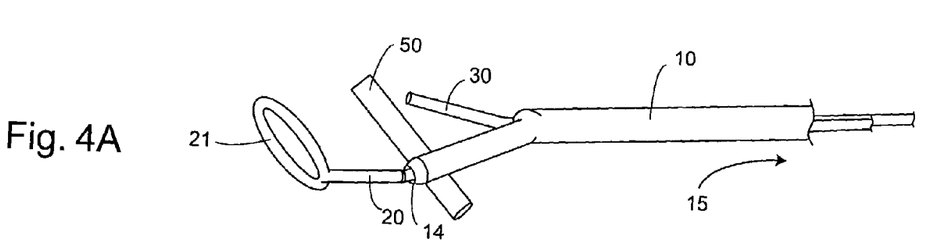
FIG. 4A, 4B and 4C are a series of schematic diagrams demonstrating a method of surrounding, snaring and grasping an object with a retrieval catheter.
Figure 4B:
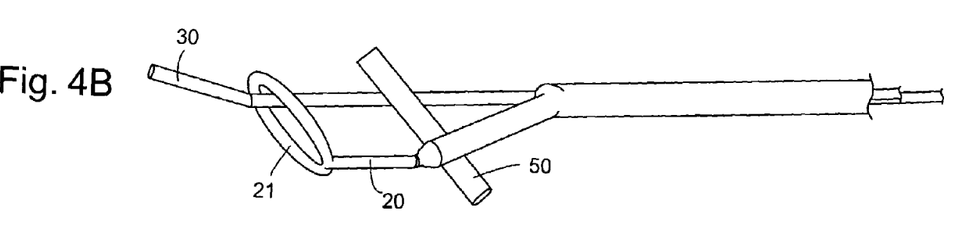
Figure 4C:
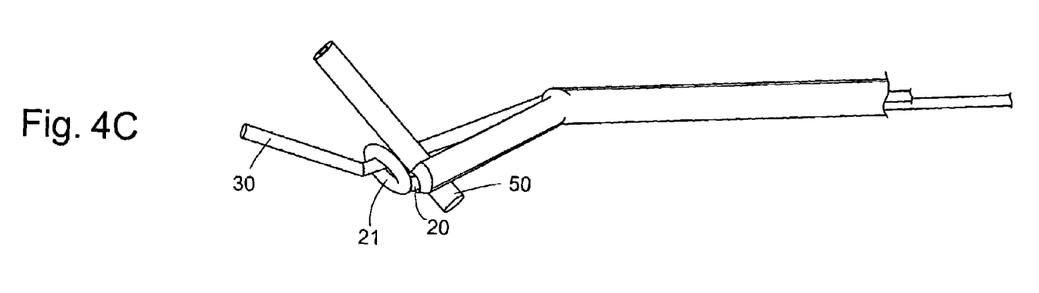

For example, the catheter can be inserted into the patient and advanced until distal port 14 of TSM 10 is adjacent to object 50. Snare wire 20 can be maneuvered around one side of object 50 and probe wire 30 can be maneuvered around another side of object 50, as shown in FIG. 4A. Probe wire 30 can be further maneuvered to thread through snare wire end loop 21, thus forming a snare, as shown in FIG. 4B. Snare wire 20 can be retracted to constrict the snare and grasp object 50, as shown in FIG. 4C. The catheter can then be withdrawn from the patient along with object 50.

Insertion and Positioning

The catheter of the invention can be used, e.g., to retrieve foreign objects from body cavities or vasculature structures. Positioning a catheter in the renal pelvis can be accomplished, e.g., by inserting the catheter in the urethra of the patient and maneuvering the catheter up through a ureter. Vasculature insertion, on the other hand, is a percutaneous procedure wherein a large hollow bore needle (sheath) is used to puncture a hole through the skin and a blood vessel. The sheath remains in place as a portal for insertion, manipulation, and withdrawal of the catheter from the blood vessel.

In one aspect of the invention, the catheter has an adjustable angle at an alignment region of the TSM. The angle is intended, e.g., to provide an offset between the snare wire and probe wire during the snaring procedure. However, during insertion and withdrawal procedures, the offset can be make passage of the catheter through narrow routes difficult. Where it is desirable to eliminate offset at the second angle, the present invention provides, e.g., an alignment wire which can be advanced into the adjustment region to straighten the angle. When the distal port of the TSM is adjacent to the object, the surgeon can withdraw the alignment wire to obtain an offset appropriate to the particular snaring procedure.

In another aspect, the catheter has a snare wire with a superelastic shape memory alloy loop. The loop can, e.g., have a collapsed shape while retracted inside the first lumen or expand to a large elliptical loop when outside the lumen. When this aspect of the invention is employed, it is often preferred, e.g., to insert the catheter with the superelastic shape memory loop collapsed within the first lumen to facilitate passage through narrow routes.

The catheter can be inserted, e.g., by a surgeon feeding the TSM through the sheath and into the vessel while observing the progress on a fluoroscope monitor. The surgeon can, e.g., maneuver the TSM to advantage by rotating and advancing the TSM while holding the grip section at the proximal end of the TSM. The surgeon can control the direction taken by the TSM by, e.g., rotating the TSM and making appropriate adjustments to the second angle, thereby directing the distal port to establish a lead that is followed by the TSM. The surgeon can continue advancing the catheter, e.g., by these and other techniques known in the art, until the distal port is positioned adjacent to the foreign object to be retrieved.

Maneuvering the Snare Wire and Probe Wire

When the distal port of the TSM has been positioned adjacent to the object, the snare wire and probe wire can be maneuvered around the object to form a snare. For example, the surgeon can select an orientation most suitable for starting wire maneuvers by rotating the TSM. The second angle of the TSM can be adjusted for a favorable offset. The snare wire can be advanced and maneuvered around one side of the object. The probe wire can be advanced and maneuvered around another side of the object and through the end loop of the snare wire to form a snare.

Adjustments can be made, e.g., to the orientation of the TSM to facilitate the upcoming wire maneuvers. For example, if the object lies horizontally across the vessel, the surgeon can rotate the TSM to an orientation wherein the wires lie one above the other so that one wire will advance over the object and the other wire will advance under the object. Additional TSM orientation adjustments can be made during the procedure as the need arises.

Adjustments can be made, e.g., to the angle of TSM second angle to facilitate the upcoming wire maneuvers. For example, if the object is particularly large, the alignment wire can be retracted from the resilient alignment region allowing the angle to increase along with the offset between the distal port and proximal port. The wider separation of the ports, relative to the object, can facilitate advancement of the wires around the object. Partial or complete retraction of the alignment wire can provide a range of beneficial offsets during the course of wire maneuvers.

Snare maneuvers start, e.g., with advancement of the end loop from a retracted position at the distal port. In one aspect of the invention, the end loop is, e.g., not wider than about the outside diameter of the distal port and is retained just outside the distal port during the insertion and positioning procedures. In another aspect, the end loop is, e.g., not wider than about the internal diameter of the distal port and is retained just inside the first lumen during the insertion and positioning procedures. In yet another aspect, the end loop is, e.g., wider than the outside diameter of the distal port but fabricated from superelastic material and retained within the first lumen during the insertion and positioning procedures. In any case, the surgeon starts wire maneuvers, e.g., by advancing the snare wire end loop toward the object from the retracted position.

Maneuvering the snare wire around the object can be as simple as advancing the wire until it extends beyond the object. In other cases, e.g., where the path around the object is convoluted, not aligned with the distal port, and/or partially blocked, the surgeon can rotate the end loop to orientations that fit an opening or are directed to the available pathway. For example, when the object is directly in front of the distal port, the snare wire, with, e.g., a 135 degree first angle, can be rotated away from the object so the wire will be directed to one side on contact with the object. After passing substantially around the side of the object, the snare wire can be rotated back toward the object, e.g., to be directed back behind the object on contact with the walls of the lodging site. Similar maneuvers can be practiced, alone or in combination with adjustments to the alignment region angle and/or TSM orientation, to advance the snare wire past a variety of complex obstacles. Finally, the snare wire can be, e.g., advanced, retracted and/or rotated to present the end loop in a position accessible to probe wire maneuvers for snare formation.

The probe wire can be maneuvered, e.g., in much the same fashion as the snare wire. Maneuvering the probe wire around the object can be as simple as advancing the wire until it extends beyond the object. In other cases, e.g., where the path around the object is convoluted, not aligned with the proximal port, and/or partially blocked, the surgeon can rotate the probe wire to orientations that are directed to the desired path. For example, where a fold of tissue partially blocks the path around the object, the probe wire, with, e.g., a 135 degree third angle, can be rotated away from the tissue so the wire will be directed away on contact with the tissue. After passing substantially around the side of the tissue, the probe wire can be rotated away from the object to be, e.g., directed to the desired side of the object (opposite the snare wire side). Finally, the probe wire can be, e.g., rotated toward the end loop of the snare wire. Similar maneuvers can be practiced, alone or in combination with TSM orientation adjustments, to advance the probe wire past a variety of complex obstacles and into the end loop to form a snare.

Withdrawing the Catheter and Object

After a snare is formed, the snare wire is retracted to constrict the snare onto the object. The catheter can be removed, along with the object, by withdrawing the TSM. The sheath can be removed and the puncture hole surgically repaired.

The snare structure consists of, e.g., a loop formed by the probe wire, the snare wire and that portion of the TSM between the distal port and the proximal port. The circumference of the snare can be reduced by retracting the snare wire into the TSM first lumen. This can be accomplished by the surgeon retracting the snare wire or by holding the snare wire stationary while the TSM is advanced toward the object.

The surgeon can apply an appropriate amount of tension on the snare wire, e.g., to establish an adequate grip on the object and/or to control location of the grip. If the object was snared in the center of its length, the surgeon can retract the TSM some distance without tension on the snare wire, thereby allowing the snare to slip along the object. Tension can then be applied to provide a grip at the end of the object, whereby the object will have less tendency to lodge in a vessel wall as it is being pulled along the catheter route.

Should the object become irreversibly entangled as it is pulled from the patient, the snare can be released, along with the rest of the catheter, from the object. To release the snare, the surgeon can, e.g., release tension on the snare wire so the snare can simply slip off the end of the object. If the end of the object is entangled or embedded along the route, the snare can be released by retracting the probe wire from the snare wire end loop, thereby freeing the two wires to be withdrawn along the two sides of the object After the catheter is withdrawn, e.g., along with the retrieved foreign object, the sheath can be removed. The small puncture hole, e.g., in the artery and skin, can be sutured for a quick recovery of the patient.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A retrieval catheter comprising:
   a tube-shaped member adapted for insertion into a patient, the tube-shaped member comprising a distal port and a proximal end;
   a proximal port on the tube-shaped member between the distal port and the proximal end;
   a first lumen extending through the tube-shaped member to the distal port;
   a second lumen extending through the tube-shaped member to the proximal port;
   a snare wire comprising an end loop, which snare wire is slidably retained by the first lumen; and,
   a probe wire slidably retained by the second lumen of the tube-shaped member.

2. The retrieval catheter of claim 1, wherein the tube-shaped member further comprises an alignment region comprising a second angle at the proximal port, thereby offsetting the distal port relative to the proximal port.

3. The retrieval catheter of claim 2, wherein the second angle comprises an angle between about 0 degrees and about 180 degrees.

4. The retrieval catheter of claim 3, further comprising:
   a third lumen extending through the alignment region within the tube-shaped member; and,
   an alignment wire slidably retained in the third lumen.

5. The retrieval catheter of claim 2, wherein the alignment region comprises a resilient material.

6. The retrieval catheter of claim 1, wherein the tube-shaped member comprises a plastic or composite material.

7. The retrieval catheter of claim 1, wherein the snare wire further comprises a first angle between about 90 degrees and about 180 degrees.

8. The retrieval catheter of claim 1, wherein the snare wire end loop comprises stainless steel, gold, or platinum.

9. The retrieval catheter of claim 1, wherein the snare wire end loop comprising a superelastic shape memory alloy.

10. The retrieval catheter of claim 9, wherein the alloy comprises nickel-titanium.

11. The retrieval catheter of claim 9, wherein the snare wire end loop comprises a collapsed shape when retained within the first lumen and an elliptical shape when outside of the lumen.

12. The retrieval catheter of claim 1, wherein the probe wire comprises a third angle.

13. The retrieval catheter of claim 12, wherein the probe wire third angle comprises an angle between about 90 degrees and about 180 degrees.

14. The retrieval catheter of claim 1, wherein the snare wire or the probe wire comprises a diameter ranging from about 0.01 inches to about 0.2 inches.

15. The retrieval catheter of claim 1, wherein the snare wire and probe wire are independently rotatable.

16. The retrieval catheter of claim 1, wherein the catheter is configured such that an object can be retrieved from the body of a patient by:
   positioning the distal port of the tube-shaped member adjacent to the object;
   advancing the snare wire end loop from the first lumen and maneuvering it around a first side of the object;
   advancing the probe wire from the second lumen and maneuvering it around a second side of the object and through the snare wire end loop to form a snare;
   retracting the snare wire into the first lumen constricting the snare around the object, thereby grasping the object; and,
   withdrawing the tube-shaped member from the patient, thereby retrieving the object from the patient.

17. A method of grasping an object inside a patient, the method comprising;
   inserting a catheter comprising a tube-shaped member into the patient, the tube-shaped member retaining a probe wire, and retaining a snare wire comprising an end loop, wherein the probe wire advances from the tube-shaped member at a proximal port between a distal port and a proximal end of the tube-shaped member;
   positioning the tube-shaped member with the snare wire and probe wire adjacent to the object;
   independently axially rotating and advancing the snare wire around a first side of the object;
   advancing the probe wire around a second side of the object, and through the end loop of the snare wire, thereby forming a snare; and,
   retracting the snare wire into the tube-shaped member to constrict the snare, thereby grasping the object.

18. The method of claim 17, further comprising independently axially rotating the probe wire, wherein the probe wire comprises a probe wire angle.

19. The method of claim 17, wherein retracting the snare wire comprises holding the snare wire stationary while advancing the tube-shaped member towards the object.

20. The method of claim 17, further comprising withdrawing the tube-shaped member from the patient, thereby retrieving the object.

21. The method of claim 17, wherein the patient is a human being or an animal.

22. The method of claim 17, wherein the object is located inside vasculature or a body cavity of the patient.

* * * * *